April 4, 1972 T. HEGG Plant Pat. 3,099
POINSETTIA PLANT
Filed April 9, 1970
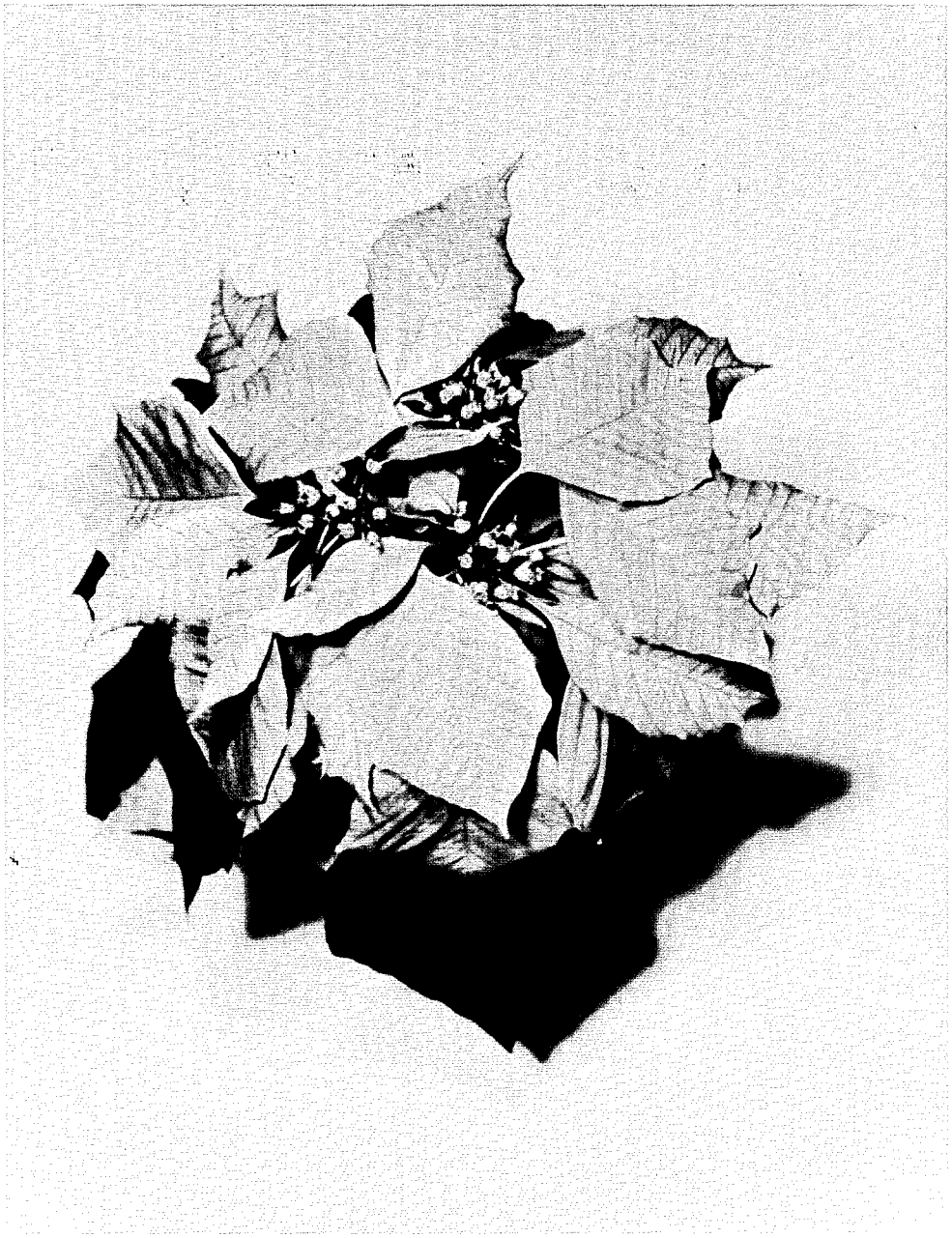
Inventor.
Thormod Hegg
By: Robb & Robb
Attorneys.

United States Patent Office

Plant Pat. 3,099
Patented Apr. 4, 1972

3,099
POINSETTIA PLANT

Thormod Hegg, Lierbyen, Norway, assignor to
Paul Ecke, Inc., Encinitas, Calif.

Filed Apr. 9, 1970, Ser. No. 27,192
Int. Cl. A01h 5/00
U.S. Cl. Plt.—86 1 Claim

The present invention relates to a new and distinct variety of *poinsettia plant*, botanically known as *Euphorbia pulcherrima*, which was discovered by me as a cultivated sport of the poinsettia variety known as "Annette Hegg" (U.S. Plant Patent No. 2962), said discovery having been made by me in my greenhouses at Lier, Norway.

At the time of my discovery aforesaid, I was growing various poinsettia varieties, including many plants of the variety "Annette Hegg." During these growing operations which were being conducted under my personal supervision and care, my attention was attracted to one particular plant among those of "Annette Hegg" which bore pink bracts instead of the normal red bracts of "Annette Hegg." Close inspection of this particular plant showed that it had sported, and I accordingly took steps to carefully preserve the sport and keep it under close observation. In due course, I also asexually reproduced the sport by vegetative cuttings taken therefrom and grown by me in my greenhouses at Lier. Continued observation and tests of the original sport and its progeny derived therefrom as aforesaid, established and confirmed that the pink bract color comes true and remains stable through succeeding propagations. Otherwise, the new sport is substantially identical in all respects to the variety "Annette Hegg." This has been further confirmed by extensive tests and observations conducted on my behalf at Encinitas, Calif., U.S.A. I am, therefore, convinced that my new pink-bracted sport represents a new and distinct poinsettia variety as evidenced by the following unique combination of characteristics which are outstanding therein and which distinguish the same from its parent, as well as from all other poinsettia varieties of which I am aware:

(1) A general similarity in most respects to the variety "Annette Hegg," including
(2) A short growing and compact plant habit;
(3) A uniform and fast rooting habit;
(4) A self-branching habit which produces multiple blooms without pinching off the terminal buds;
(5) Attractive green foliage;
(6) Distinctive, attractive and stable pink bracts instead of red bracts like "Annette Hegg"; and
(7) Long-lasting plant qualities.

The accompanying drawing shows a typical specimen plant of my new poinsettia variety as illustrated in color.

Although, except for the bract color, the details of the new variety substantially conform to the description embodied in U.S. Plant Patent No. 2962, to which reference may be readily had, the following brief description is given for convenience, with color terminology in accordance with Wilson's Horticultural Colour Chart, except where general color terms of ordinary dictionary significance are obvious:

Locality where grown and observed: Lier, Norway, and also Encinitas, Calif., U.S.A.
Parentage: Sport of "Annette Hegg."
Propagation: Holds its distinguishing characteristics through succeeding propagations by vegetative cuttings.
Form: Short growing; compact.
Habit of growth: Self-branching; contrary to other poinsettia varieties, does not require pinching off terminal buds to produce multiple blooms; as many as ten side shoots develop without pinching, but when pinched, the side shoots become even more vigorous.
Rooting habit: Very uniform and very fast.
Blooming habit: The blooming is more predictable than other known varieties, and it is a "9-week" variety.
Blooming season: Blooms predictably and in time for Christmas season and well beyond through at least the month of April; is also a good variety for flowering in spring, summer and autum.
Foliage: The shape of the leaves vary a little from other known varieties.
*Shape.*—Most typical leaves are more ovate—acuminate, and only seldom lobed.
*Color.*—New foliage—Upper side—Pod Green, Plate 061. Lower side—Pod Green, Plate 061/1. Old foliage—Upper side—Spinach Green,, Plate 0960. Lower side—Spinach Green, Plate 0960/2.
Bracts: Obovate; relatively broad. Color—Near Delft Rose, Plate 020/2.
Reproductive organs:
*Stamens.*—Quite numerous; from about ⅛ inch to ¼ inch long. Color—Currant Red, Plate 821/2.
*Pollen.*—Color—Canary Yellow, Plate 2.
*Styles.*—Color—Blood Red, Plate 820.
*Ovaries.*—Color—Scheele's Green, Plate 860/1.
*Nectar cups.*—Color—Lemon Yellow, Plate 4/1.

I claim:

1. A new and distinct variety of poinsettia plant, substantially as herein shown and described, characterized particularly as to novelty by the unique combination of a general similarity in most respects to the variety "Annette Hegg," including a short growing and compact plant habit, a uniform and fast rooting habit, a self-branching habit which produces multiple blooms without pinching off the terminal buds, attractive green foliage, distinctive, attractive and stable pink bracts instead of red bracts like "Annette Hegg," and long-lasting plant qualities.

No references cited.

ROBERT E. BAGWILL, Primary Examiner